(12) United States Patent
Haras et al.

(10) Patent No.: US 7,573,980 B2
(45) Date of Patent: Aug. 11, 2009

(54) METHOD FOR OPERATING AN X-RAY COMPUTER TOMOGRAPH

(75) Inventors: Gabriel Haras, Mücke (DE); Peter Aulbach, Kersbach (DE)

(73) Assignee: Siemens Aktiengesellschaft, Munich (DE)

( * ) Notice: Subject to any disclaimer, the term of this patent is extended or adjusted under 35 U.S.C. 154(b) by 119 days.

(21) Appl. No.: 11/642,891

(22) Filed: Dec. 21, 2006

(65) Prior Publication Data
US 2007/0165771 A1 Jul. 19, 2007

(30) Foreign Application Priority Data
Dec. 22, 2005 (DE) .................. 10 2005 061 559

(51) Int. Cl.
*H05G 1/58* (2006.01)
*A61B 6/03* (2006.01)

(52) U.S. Cl. .................. 378/116; 378/15; 378/20; 378/115

(58) Field of Classification Search ............ 378/4, 378/9, 15, 16, 115, 116, 196, 197, 20
See application file for complete search history.

(56) References Cited

U.S. PATENT DOCUMENTS

| | | | | |
|---|---|---|---|---|
| 5,247,556 A | | 9/1993 | Eckert et al. | |
| 5,373,543 A | * | 12/1994 | Ackermann et al. | 378/20 |
| 5,400,378 A | * | 3/1995 | Toth | 378/16 |
| 5,966,422 A | * | 10/1999 | Dafni et al. | 378/9 |
| 5,999,587 A | * | 12/1999 | Ning et al. | 378/4 |
| 6,031,888 A | * | 2/2000 | Ivan et al. | 378/20 |
| 6,061,420 A | * | 5/2000 | Strong et al. | 378/4 |
| 6,173,033 B1 | | 1/2001 | Klingenbeck-Regn et al. | |
| 6,266,553 B1 | * | 7/2001 | Fluhrer et al. | 600/428 |
| 6,512,808 B2 | * | 1/2003 | Klingenbeck-Regn | 378/18 |
| 6,614,871 B1 | | 9/2003 | Kobiki et al. | |
| 6,928,137 B2 | * | 8/2005 | Bruder et al. | 378/4 |
| 6,990,170 B2 | * | 1/2006 | Sugihara et al. | 378/15 |
| 7,142,630 B2 | * | 11/2006 | Suzuki | 378/16 |

FOREIGN PATENT DOCUMENTS

| | | |
|---|---|---|
| DE | 41 03 588 C1 | 5/1992 |
| DE | 197 21 535 A | 11/1998 |
| EP | 0 531 993 B1 | 1/1998 |
| EP | 0 919 185 A1 | 6/1999 |

OTHER PUBLICATIONS

German Office Action, Oct. 18, 2006.

* cited by examiner

*Primary Examiner*—Allen C. Ho
(74) *Attorney, Agent, or Firm*—Harness, Dickey & Pierce, P.L.C.

(57) ABSTRACT

A selectable mode of operation is disclosed for an X-ray computer tomograph for producing angiographical images. A patient accommodated on a couch is not moved relative to the measuring system in the z-direction, the entire area to be examined is irradiated at a prescribed first angle of rotation of the measuring system, and the X-ray radiation emerging from the area to be examined is detected isochronously using a matrix detector.

24 Claims, 4 Drawing Sheets

METHOD FOR OPERATING AN X-RAY COMPUTER TOMOGRAPH

PRIORITY STATEMENT

The present application hereby claims priority under 35 U.S.C. §119 on German patent application number DE 10 2005 061 559.7 filed Dec. 22, 2005, the entire contents of which is hereby incorporated herein by reference.

FIELD

Embodiments of the invention generally relate to a method for operating an X-ray computer tomograph and/or to an X-ray computer tomograph.

BACKGROUND

DE 41 03 588 C1 and EP 0 531 993 B1 describe an X-ray computer tomograph having a rotatable measuring system in which an X-ray source and a detector are arranged in an opposite arrangement so as to be able to rotate about a common axis. To produce sectional images, a patient accommodated on a couch is irradiated in spiral fashion. The X-ray radiation emerging from the patient is detected using the detector and is then converted into a sectional image by, means of computer using a suitable algorithm. To produce a topographical overview shot or a silhouette, a further algorithm is provided which can be used to produce the desired silhouette from the image data for a prescribed angular position which are recorded together with the respective angular position of the measuring system.

The image data used to produce the silhouette are not captured at the same time rather in steps. In this context, the patient is moved in the z-direction. Known X-ray computer tomographs are not suitable for producing angiographical images. A contrast agent administered to the patient changes its distribution in the body over time. When the image data are recorded in steps or at different times, the contrast agent cannot be shown or at least cannot be shown exactly.

EP 0 919 185 A1 discloses an X-ray computer tomograph which is combined with a C-arc X-ray apparatus in order to produce angiographical images. The known X-ray computer tomograph requires a high level of production outlay. To change between the X-ray diagnosis methods, the patient needs to be moved from one X-ray apparatus to the other. This requires the provision of a specially designed couch which can be moved a long way in the z-direction. Apart from this, moving patients with life-threatening injuries, in particular, results in a time delay which is a drawback from the point of view an emergency doctor.

DE 197 21 535 A1 describes an X-ray computer tomograph in which a silhouette is produced by locking the measuring system in a prescribed angular position and then moving the patient in the z-direction. The image data recorded in succession for various z-positions are then processed further using a computer to produce the silhouette. In this context, the measuring system may also comprise a multirow detector or a matrix detector. Using such a matrix detector, a striped silhouette may be recorded. When the patient moves in the z-direction, each point on the patient is detected a plurality of times in line with the number of detector times. This allows the silhouette to be reconstructed particularly quickly when using a deblurring filter.

SUMMARY

In at least one embodiment of the invention a method is specified for operating an X-ray computer tomograph, an X-ray computer tomograph specified and/or a use therefor is specified, which allow not only the production of sectional images but also the production of angiographical images.

On the basis of one stipulation of at least one embodiment of the invention, a method for operating an X-ray computer tomograph has provision that, in a selectable second mode of operation for producing angiographical images, the patient accommodated on the couch is not moved relative to the measuring system in the z-direction, the entire area to be examined is irradiated at a prescribed first angle of rotation of the measuring system, and the X-ray radiation emerging from the area to be examined is detected isochronously using the matrix detector.

The proposed method, in at least one embodiment, allows both sectional images and angiographical images to be produced just with one X-ray computer tomograph. This no longer requires the provision of a special C-arc X-ray apparatus and removal of the patient. This allows rapid diagnosis.

In accordance with one advantageous refinement of at least one embodiment, in the first mode of operation, the area to be examined is irradiated in spiral fashion by moving the patient in the z-direction while the measuring system is rotated. This allows particularly rapid production of the sectional images.

In the second mode of operation, the measuring system can be secured at the prescribed first angle of rotation. In accordance with one particularly advantageous refinement of at least one embodiment, the second mode of operation involves the measuring system being rotated and the X-ray radiation being detected when the prescribed first angle of rotation is reached. This makes it possible, when changing over from the first to the second mode of operation, to dispense with slowing down and speeding up the measuring system again, which makes it possible to achieve particularly rapid production of angiographical images.

In accordance with another advantageous refinement of at least one embodiment, the signals detected when the prescribed first angle of rotation is reached are stored and then read in order to produce the angiographical image. For this purpose, a special memory may be provided. This allows sectional images and angiographical images to be produced more or less isochronously.

In accordance with one advantageous refinement of at least one embodiment, in the second mode of operation, a second angiographical image is produced at a prescribed second angle of rotation. This allows particularly accurate detection of the physical arrangement of the vessels to be examined.

In accordance with one development of at least one embodiment of the invention, the measuring system comprises a second X-ray source and a second matrix detector in an opposite arrangement with respect to the axis of rotation, the second X-ray source being mounted with an offset from the first X-ray source by an angle phi. The angle phi is normally 90°. This allows isochronous detection of sectional images and/or angiographical images at various angles. This makes it possible to show the movement of the heart, for example.

Expediently, the first and second modes of operation are controlled using a computer program. The computer program may include a selection section which allows the respective desired mode of operation to be selected. The selection section expediently allows parameters to be set or input. Thus, by way of example, the first and/or the second angle of rotation can be set using a setting field provided on a screen. The setting field may include function panels for changing over between the first and the second mode of operation. In addition, it is also possible to display the first and/or second angiographical image on the screen. The simultaneous use of the screen both for displaying the images produced and for controlling the X-ray computer tomograph allows particularly simple and rapid handling.

In accordance with another refinement of at least one embodiment, a 3D angiographical image is produced from the first and second angiographical images using a prescribed algorithm and is displayed on the screen. This provides the treating doctor with particularly comprehensive information about the vessel to be examined.

In accordance with one particularly advantageous refinement, the first and/or second matrix detector used is a flat panel image detector. Such a flat panel image detector allows coverage in the z-direction over a great distance of more than 10 cm, preferably more than 15 cm, particularly preferably more that 20 cm. This allows an angiographical image to be produced with great coverage in the z-direction without moving the patient in the z-direction. Instead of flat panel image detectors, it is naturally also possible to use other suitable matrix detectors with appropriately great coverage in the z-direction.

In accordance with another development of at least one embodiment of the invention, in a selectable third mode of operation for producing topographical overview images, the patient accommodated on the couch is moved relative to the measuring system in the z-direction, the X-ray radiation emerging from the area to be examined is detected using the matrix detector at a prescribed third angle of rotation, and this is used to produce the topographical overview image. A topographical overview image or silhouette of this kind can be produced using conventional methods. To this end, reference is made by way of example to the prior art cited in the introduction.

To improve or simplify handling further, it is advantageously possible for at least one sectional image, the topographical overview image and at least one angiographical image to be displayed on the screen at the same time.

In accordance with another refinement of at least one embodiment of the invention, further angiographical images are produced with angulations about a further axis of rotation, differing from the axis of rotation, using a C-arc X-ray appliance which can be controlled using the computer program. Combination with a C-arc X-ray appliance allows production of further angiographical images with further angulations, which means that it is possible to dispense with removing the patient.

On the basis of a further stipulation of at least one embodiment of the invention, the computer in an X-ray computer tomograph is provided with a computer program for carrying out at least one embodiment of the inventive method. The inventive computer program allows the measuring system to be controlled, in particular, so that the first, second and possibly third modes of operation are thus made possible. In this context, the computer program is automatically used for automatically controlling the function sequences required for implementing the respective mode of operation.

In accordance with another refinement of at least one embodiment of the invention, the X-ray computer tomograph has a device for storing the signals detected when the prescribed first angle of rotation is reached. This allows particularly rapid production of the desired angiographical images. It is therefore also possible for the signals for producing the angiographical images not to be retrieved until a later time.

The measuring system may include a second X-ray source and a second matrix detector in an opposite arrangement with respect to the axis of rotation, the second X-ray source being mounted with an offset from the first X-ray source by an angle phi. The angle phi denotes an angle by which the two X-ray sources are arranged offset from one another in a scan plane, which is usually at right angles to the z-direction. X-ray computer tomographs having two X-ray sources and respective opposite matrix detectors are known from the prior art. They can likewise easily be redesigned, e.g. by changing the software, so that they can be used to implement at least one embodiment of the present invention. Thus, it is possible not only to produce sectional images and angiographical images but also to observe the movement of the heart, for example.

The first and/or second matrix detector may be a flat panel image detector. It goes without saying that it is also possible to use other detectors with a sufficient extent and resolution in the z-direction.

In accordance with one refinement of at least one embodiment, the purpose of producing further angiographical images with angulations about a further axis of rotation, differing from the axis of rotation, is served by providing a C-arc X-ray appliance which can be controlled using the computer program. This allows the isochronous production of angiographical images with various angulations in time-saving fashion. Controlling the C-arc X-ray appliance using the computer program simplifies handling. The treating doctor can therefore create a diagnosis quickly and without removing the patient. This is advantageous particularly for life-threatening head injuries.

On the basis of a further stipulation of at least one embodiment of the invention, the use of an X-ray computer tomograph having a computer and a rotatable measuring system which can be controlled thereby, and which includes a first X-ray source and a first matrix detector in an opposite arrangement with respect to an axis of rotation, for producing angiographical images is proposed.

BRIEF DESCRIPTION OF THE DRAWINGS

Examplary embodiments of the invention are explained in more detail below with reference to the drawings, in which.

DETAILED DESCRIPTION OF THE EXAMPLE EMBODIMENTS

Figure 1:
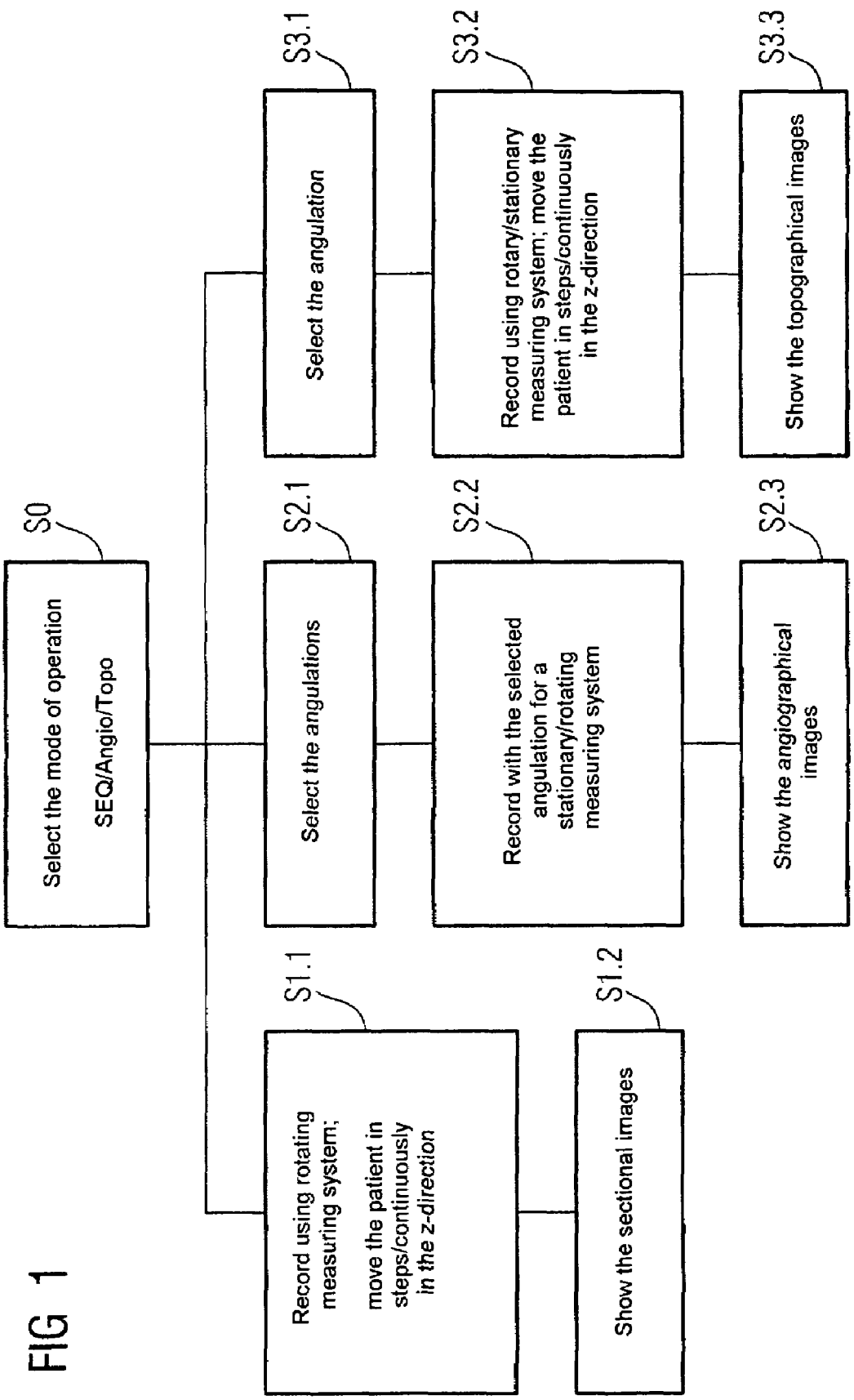
FIG. 1 shows a schematic overview of fundamental functions of the computer program.

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described.

FIG. 1 shows an overview of the fundamental functions which can be executed using a computer provided with the computer program in combination with the hardware of an X-ray computer tomograph.

The computer program includes a first selection section. In a first selection section, the user can choose, in step S0, between a conventional first mode of operation SEQ for producing sectional images, a second mode of operation Angio for producing angiographical images and a conventional third mode of operation Topo for producing topographical overview shots.

When the first mode of operation is selected, a measuring system in the X-ray computer tomograph is made to move in rotation about an axis of rotation, which runs parallel to a z-axis, for example, in step S1.1. A patient accommodated on a couch so that the longitudinal axis of his body is essentially parallel to the z-axis is irradiated in rotating fashion using the measuring system. In this case, the patient is moved either in steps or continuously in the z-direction, so that sectional images are produced in succession along the z-axis. The sectional images can be shown on a screen, for example, in step S1.2.

When the second mode of operation Angio is selected, an angiographical image or silhouette of a body section of the patient is produced at a prescribed angle of irradiation or with a prescribed angulation. The relevant angulation can be preset or can be changed in a second selection section in step S2.1. It is also possible to produce a plurality of angiographical images with various angulations by setting appropriate different angles of irradiation in the second selection section.

Next, the patient is irradiated with the prescribed angulation(s) in step S2.2. The attenuated radiation emerging from the patient with the respective angulation is detected with simultaneous spatial resolution using the matrix detector. The captured image data are then used to produce a silhouette while omitting the algorithm which is required for producing sectional images in the first mode of operation. In this case, the patient is not moved in the z-direction. The angiographical images produced can be shown on the screen in step 2.3.

For the purpose of irradiation with the prescribed angulation, the measuring system can be secured or else rotated. If the measuring system is rotated then the image data recorded with the respective angulation are read from a memory and are processed further to produce a silhouette. To speed up this method, the recorded image data can be copied to a special memory provided for this purpose and can be read from this memory and processed further in order to produce the silhouettes.

To produce a topographical overview shot, a prescribed further angulation can be confirmed or changed in a third selection section in step S3.1. In a conventional method, the patient can then be irradiated with the prescribed further angulation—in similar fashion to in the case of the second mode of operation—either using a secured measuring system or using a rotating measuring system. In this case, however, the patient is moved in the z-direction relative to the measuring system. The silhouettes recorded in the process in step S3.2 can be assembled to form a topographical image using a conventional algorithm. The topographical image can be shown on the screen in step S3.3.

Figure 2:
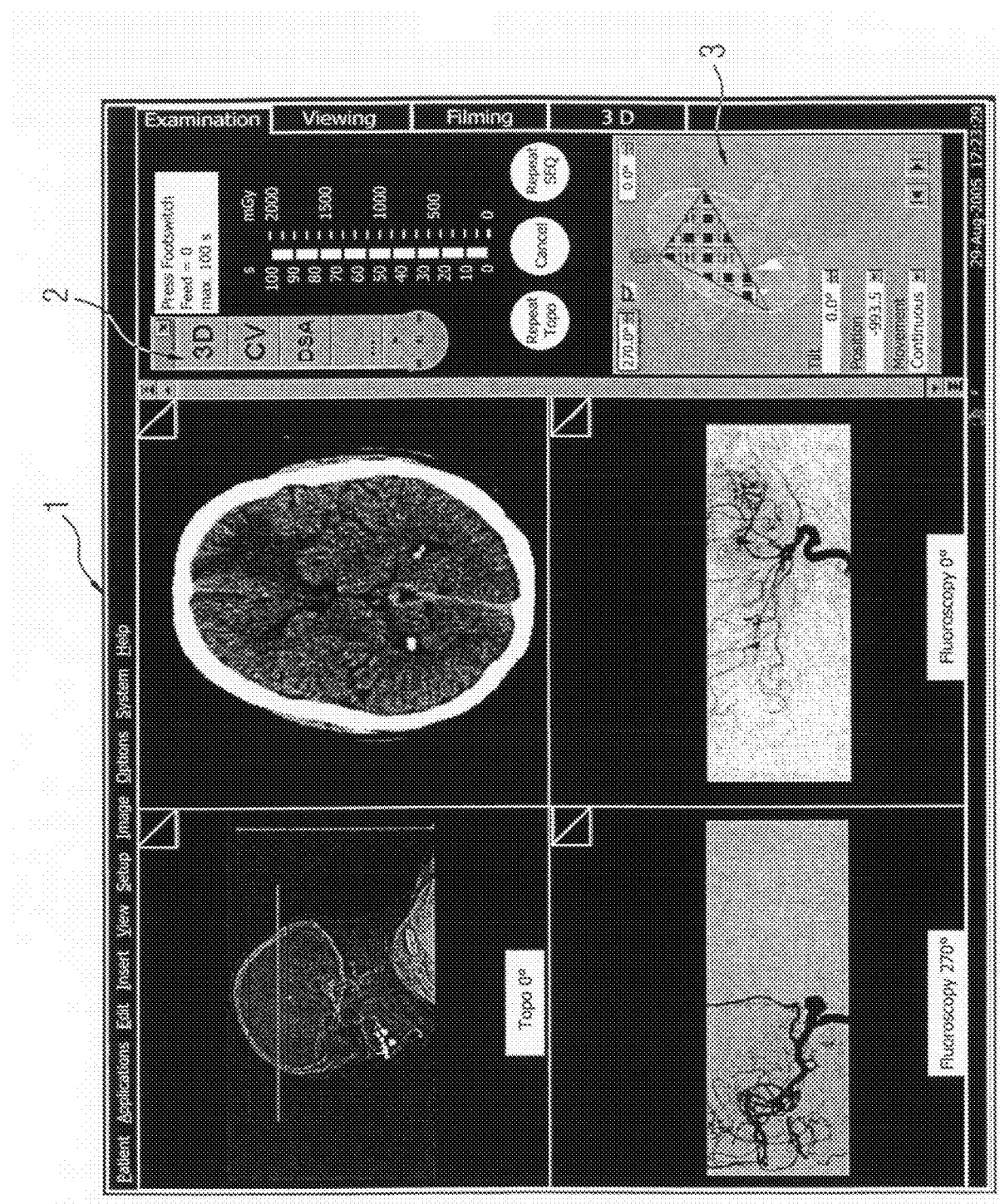
FIG. 2 shows a screenshot.

FIG. 2 shows a screen 1 as an example. The screen 1 has a first selection 2 which can be used to choose between a first mode of operation for producing sectional images—in this case the button "CV"—and a second mode of operation for producing angiographical images—in this case the button "DSA". In a second selection section 3, two different angulations may be set in order to produce angiographical images. The angiographical images produced with the angulations, in this case 0° and 270°, are shown on the left of the screen 1 next to the second selection section. On the left next to the first selection section 2, a sectional image produced in the first mode of operation and a topographical overview image are shown. The topographical overview image additionally indicates the sectional position of the sectional image shown next to it.

Simultaneously showing the images recorded in the first, second and third modes of operation on one and the same screen 1 together with the selection sections 2 and 3 allows particularly simple, effective and rapid handling of the proposed X-ray computer tomograph.

Figure 3:
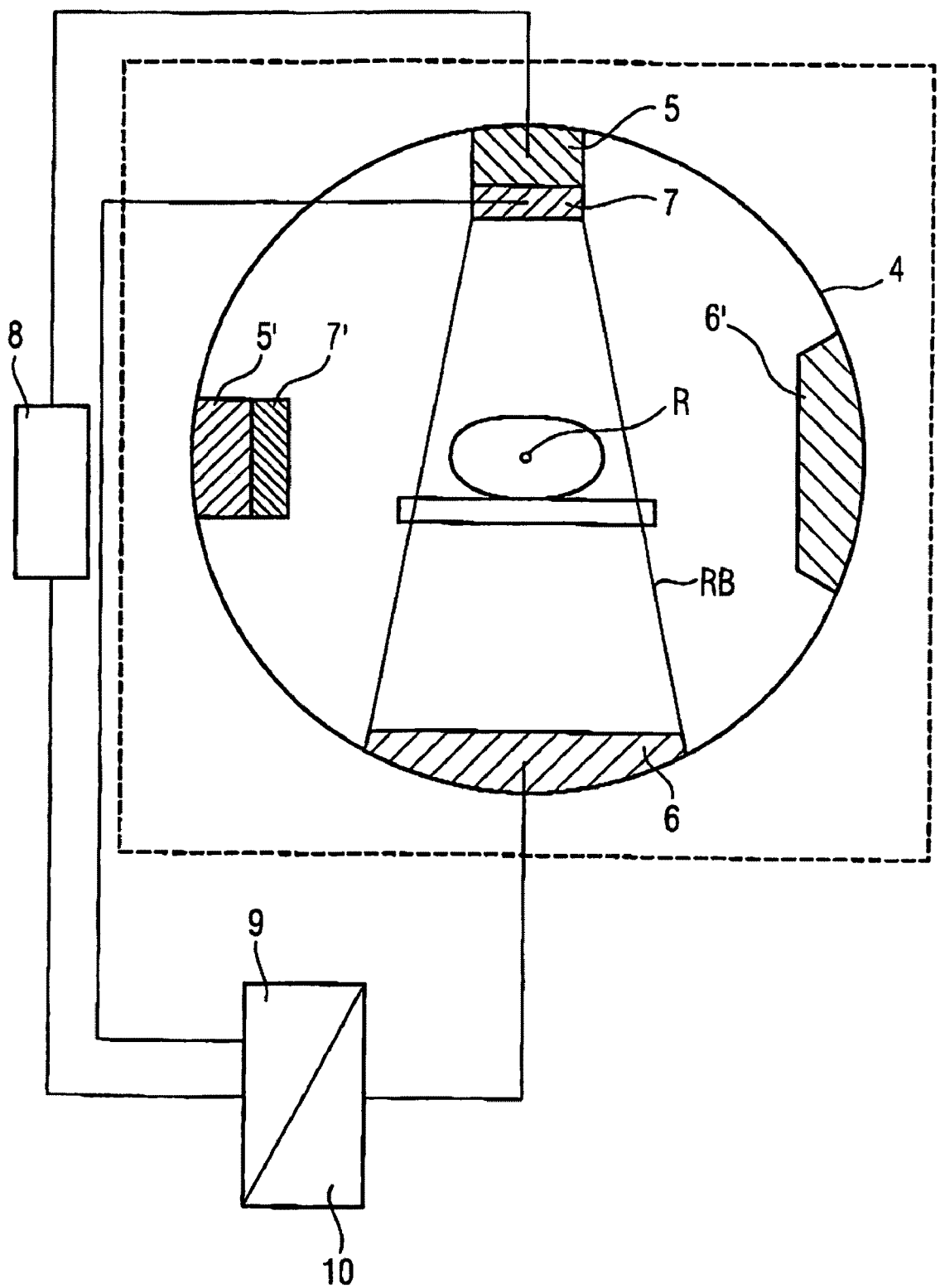
FIG. 3 shows a schematic view of a rotatable measuring system.

FIG. 3 schematically shows a gantry for an X-ray computer tomograph having a rotatable measuring system 4. The rotatable measuring system 4 includes an X-ray source 5 and, arranged opposite, a matrix detector 6. In the beam path, the X-ray source 5 has a downstream diaphragm 7 which can be used to set a thickness for the stopped X-ray beam RB also in the z-direction, in particular. An axis of rotation for the rotatable measuring system 4 is denoted by the reference symbol R. The rotatable measuring system may also include a second X-ray source 5', a second diaphragm 7' of the second X-ray source 5' and a second matrix detector 6'.

The X-ray tube 5 is connected to a high voltage generator 8 which can be actuated by way of a controller 9, for example a computer. The diaphragm 7, which can preferably be set electrically, is likewise connected to the controller 9. The matrix detector 6 is connected to an electronic memory 10 for storing the images or measured values recorded thereby. The electronic memory 10 may be a component part of the computer. The connections of the second X-ray source 5', the second diaphragm 7' of the second X-ray source 5' and the second matrix detector 6' are not shown, but may be connected to the controller 9 and the electronic memory 10 in a similar manner as the X-ray tube 5, diaphragm 7 and matrix detector 6, respectively.

To produce angiographical images during rotation of the rotating measuring system 4, the controller 9 is first of all used to set the desired angulation(s) and the position corresponding thereto in the z-direction. When the set angulation and the prescribed z-position are reached, an angiographical "silhouette" is then recorded. For this purpose, the diaphragm 7 is preferably opened to the extent that the stopped X-ray beam hits the matrix detector 6 over the entire area. In addition, the controller 9 can be used to actuate the high voltage generator 8 such that an X-ray intensity which is suitable for producing angiographical images is produced with the X-ray source 5.

It has been found to be advantageous to record angiographical images while the rotatable measuring system 4 is rotating. This eliminates the need for time-consuming braking and speeding up of the rotatable measuring system 4. In addition, it is not necessary to set the rotatable measuring system 4 to a prescribed particular angle. The recording which is required in order to produce the angiographical images can instead be made during rotation when the prescribed angle or the prescribed angulation is reached.

To change over to the first mode of operation for producing sectional images, it is merely necessary to process the images or signals recorded by the matrix detector 6 in the manner which is conventional for producing CT images using suitable algorithms. Apart from this, it is additionally possible to set the power of the X-ray source 5 and the diaphragm 7 in a manner which is optimum for producing CT images. Furthermore, CT images can be produced by additionally moving the patient accommodated on the couch relative to the measuring system 4 in the z-direction, so that he is irradiated in spiral fashion.

Figure 4:
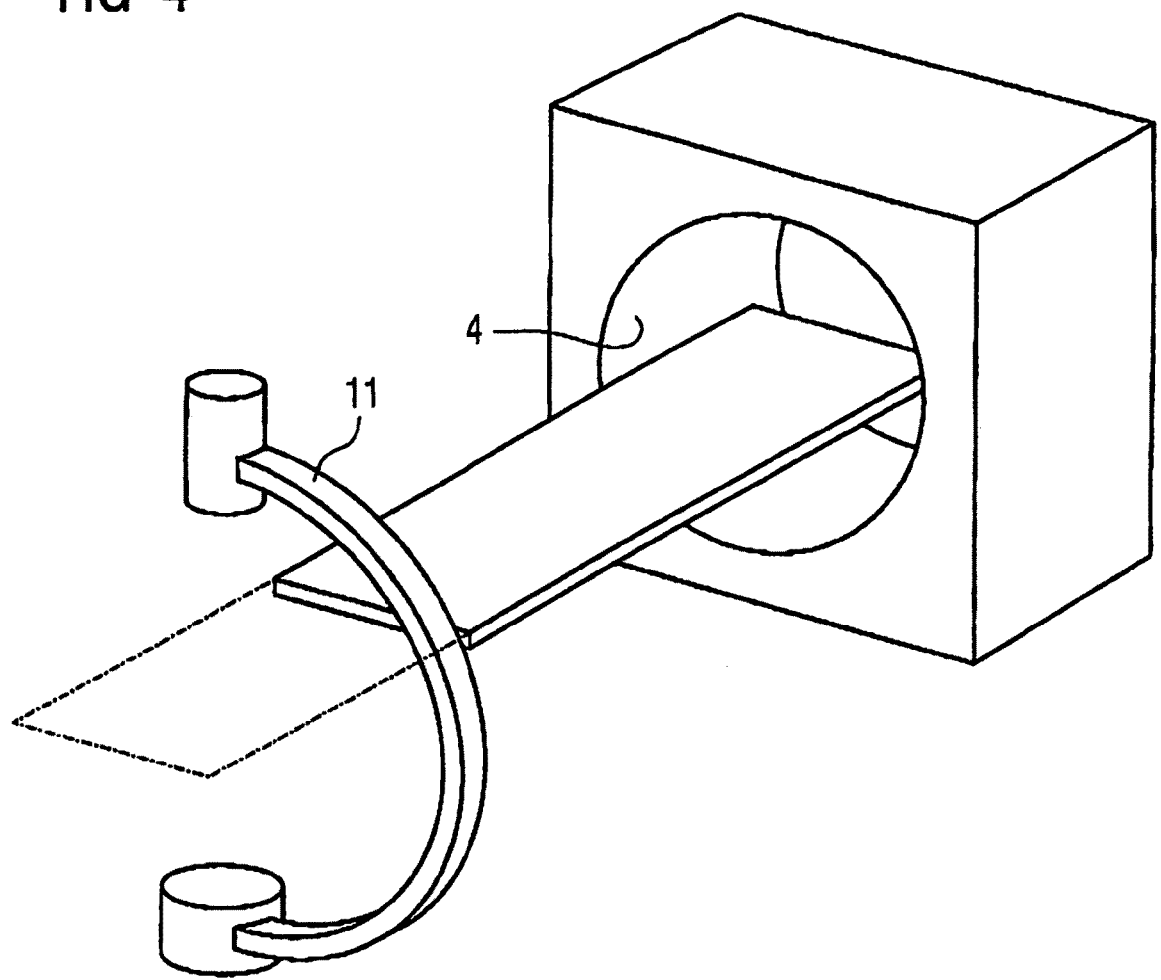
FIG. 4 shows a perspective view of a C-arc X-ray appliance.

FIG. 4 illustrates an example embodiment of the rotatable measuring system 4 used in conjunction with a C-arc X-ray appliance 11.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDS; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for operating an X-ray computer tomograph including a rotatable measuring system which includes a first X-ray source having a downstream diaphragm and a first matrix detector in an opposite arrangement with respect to an axis of rotation, wherein the first matrix detector is a flat panel image detector, comprising:

moving, in a selectable first mode of operation for producing sectional images, a patient accommodated on a couch relative to the measuring system in the z-direction, irradiating an area to be examined in circulating fashion by rotating the measuring system, and detecting the X-ray radiation emerging from the area to be examined using the first matrix detector;

not moving, in a selectable second mode of operation for producing angiographical images, the patient accommodated on the couch relative to the measuring system in the z-direction, irradiating the entire area to be examined at a first angle of rotation of the measuring system by opening said diaphragm to an extent that an irradiated X-ray beam hits the first matrix detector over the entire area to be examined, and detecting the X-ray radiation emerging from the area to be examined isochronously using the first matrix detector; and moving, in a selectable third mode of operation for producing topographical overview images, the patient accommodated on the couch relative to the measuring system in the z-direction, irradiating an area to be examined, detecting the x-ray radiation emerging from the area to be examined using the first matrix detector at a third angle of rotation, and using the detected x-ray radiation to produce the topographical overview image.

2. The method as claimed in claim 1, wherein, in the first mode of operation, the area to be examined is irradiated in spiral fashion by moving the patient in the z-direction while the measuring system is rotated.

3. The method as claimed in claim 2, wherein the second mode of operation involves the measuring system being secured at the first angle of rotation.

4. The method as claimed in claim 2, wherein the second mode of operation involves the measuring system being rotated and the X-ray radiation being detected when the first angle of rotation is reached.

5. The method as claimed in claim 1, wherein the second mode of operation involves the measuring system being secured at the first angle of rotation.

6. The method as claimed in claim 1, wherein the second mode of operation involves the measuring system being rotated and the X-ray radiation being detected when the first angle of rotation is reached.

7. The method as claimed in claim 1, wherein the signals detected when the first angle of rotation is reached are stored and then read in order to produce the angiographical image.

8. The method as claimed in claim 1, wherein, in the second mode of operation, a second angiographical image is produced at a second angle of rotation.

9. The method as claimed in claim 8, wherein at least one of the first and second angiographical images are displayable on a screen.

10. The method as claimed in claim 1, wherein the measuring system includes a second X-ray source and a second matrix detector in an opposite arrangement with respect to the axis of rotation, the second X-ray source being mounted with an offset from the first X-ray source by an angle phi.

11. The method as claimed in claim 10 wherein the second matrix detector is a flat panel image detector.

12. The method as claimed in claim 1, wherein the first and second modes of operation are controlled using a computer program, at least one of the first and a second angle of rotation being able to be set using a setting field provided on a screen.

13. The method as claimed in claim 1, wherein a setting field includes function panels for changing over between the first and the second mode of operation.

14. The method as claimed in claim 1, wherein at least one sectional image, a topographical overview image and at least one angiographical image are displayed on a screen at the same time.

15. The method as claimed in claim 1, wherein further angiographical images are produced using a C-arc X-ray appliance which is controllable using the computer program.

16. An X-ray computer tomograph, comprising:
a couch;
a computer; and
a rotatable measuring system, controllable by the computer, including a first X-ray source having a downstream diaphragm and a first matrix detector in an opposite arrangement with respect to an axis of rotation, wherein the first matrix detector is a flat panel image detector, the computer being provided with a computer program, which, when executed on the computer, carries out the following,
moving, in a selectable first mode of operation for producing sectional images, a patient accommodated on the couch relative to the measuring system in the z-direction, irradiating an area to be examined in circulating fashion by rotating the measuring system, and detecting the X-ray radiation emerging from the area to be examined using the first matrix detector;
not moving, in a selectable second mode of operation for producing angiographical images, the patient accommodated on the couch relative to the measuring system in the z-direction, irradiating the entire area to be examined at a first angle of rotation of the measuring system by opening said diaphragm to an extent that an irradiated X-ray beam hits the first matrix detector over the entire area to be examined, and detecting the X-ray radiation emerging from the area to be examined isochronously using the first matrix detector; and
moving, in a selectable third mode of operation for producing topographical overview images, the patient accommodated on the couch is moved relative to the measuring system in the z-direction, the X-ray radiation emerging from the area to be examined is detected using the first matrix detector at a third angle of rotation, and the detected X-ray radiation is used to produce the topographical overview image.

17. The X-ray computer tomograph as claimed in claim 16, further comprising a device for storing the signals detected when the first angle of rotation is reached.

18. The X-ray computer tomograph as claimed in claim 17, wherein the measuring system comprises a second X-ray source and a second matrix detector in an opposite arrangement with respect to the axis of rotation, the second X-ray source being mounted with an offset from the first X-ray source by an angle phi.

19. The X-ray computer tomograph as claimed in claim 18, wherein the second matrix detector is a flat panel image detector.

20. The x-ray computer tomograph as claimed in claim 17, wherein producing further angiographical images is served by providing a C-arc X-ray appliance which can be controlled using the computer program.

21. The X-ray computer tomograph as claimed in claim 16, wherein the measuring system comprises a second X-ray source and a second matrix detector in an opposite arrangement with respect to the axis of rotation, the second X-ray source being mounted with an offset from the first X-ray source by an angle phi.

22. The X-ray computer tomograph as claimed in claim 21, wherein the second matrix detector is a flat panel image detector.

23. The x-ray computer tomograph as claimed in claim 16, wherein producing further angiographical images is served by providing a C-arc X-ray appliance which can be controlled using the computer program.

24. A computer readable medium including program segments for, when executed on a computer device of the computer tomograph, causing the computer tomograph to implement the method of claim 1.

* * * * *